United States Patent
Mitsumori

(10) Patent No.: US 11,823,788 B2
(45) Date of Patent: Nov. 21, 2023

(54) TASK ASSIGNMENT SUPPORTING APPARATUS, TASK ASSIGNMENT SUPPORTING SYSTEM, AND TASK ASSIGNMENT SUPPORTING METHOD

(71) Applicant: Canon Medical Systems Corporation, Otawara (JP)

(72) Inventor: Keita Mitsumori, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 143 days.

(21) Appl. No.: 17/130,314

(22) Filed: Dec. 22, 2020

(65) Prior Publication Data

US 2021/0202071 A1 Jul. 1, 2021

(30) Foreign Application Priority Data

Dec. 26, 2019 (JP) ................................ 2019-236252

(51) Int. Cl.
*G16H 30/20* (2018.01)
*G06T 7/00* (2017.01)
*G16H 50/20* (2018.01)
*G16H 30/40* (2018.01)

(52) U.S. Cl.
CPC ............ *G16H 30/20* (2018.01); *G06T 7/0012* (2013.01); *G16H 30/40* (2018.01); *G16H 50/20* (2018.01)

(58) Field of Classification Search
CPC ....... G16H 30/20; G16H 50/00; G06T 7/0012
See application file for complete search history.

(56) References Cited

U.S. PATENT DOCUMENTS

| 7,995,815 | B2* | 8/2011 | Nekrich | G16H 40/20 |
| | | | | 382/128 |
| 8,073,713 | B2* | 12/2011 | Thorne | G06Q 10/06398 |
| | | | | 705/2 |
| 9,558,323 | B2* | 1/2017 | Jester | G06Q 10/063118 |
| 10,552,672 | B2 | 2/2020 | Iwase et al. | |

(Continued)

FOREIGN PATENT DOCUMENTS

| JP | 2006-65483 A | 3/2006 |
| JP | 2006-268075 A | 10/2006 |

(Continued)

OTHER PUBLICATIONS

Office Action dated Jul. 3, 2003, issued in corresponding Chinese patent application No. 202011534447.9.

(Continued)

*Primary Examiner* — John Villecco
*Assistant Examiner* — Courtney Joan Nelson
(74) *Attorney, Agent, or Firm* — Oblon, McClelland, Maier & Neustadt, L.L.P.

(57) ABSTRACT

According to one embodiment, a task assignment supporting apparatus includes processing circuitry. The processing circuitry manages types of image reading preferences indicating types of image reading tasks preferred by each radiologist. The processing circuitry acquires an image reading order and a type of image reading order indicating a type of image reading task required for the image reading order. The processing circuitry assigns to the image reading order a radiologist with a type of image reading preference corresponding to the type of image reading order.

14 Claims, 15 Drawing Sheets

(56) References Cited

U.S. PATENT DOCUMENTS

| | | | |
|---|---|---|---|
| 2012/0070811 A1* | 3/2012 | Fox .................. | G09B 19/00 |
| | | | 434/262 |
| 2015/0347694 A1* | 12/2015 | Chung ................ | G16H 30/40 |
| | | | 705/3 |
| 2016/0350919 A1* | 12/2016 | Steigauf .............. | G06V 10/82 |

FOREIGN PATENT DOCUMENTS

| | | | |
|---|---|---|---|
| JP | 2009-75951 A | 4/2009 |
| JP | 2009-157527 A | 7/2009 |
| JP | 2010-204993 A | 9/2010 |
| JP | 2014-67229 A | 4/2014 |
| JP | 2016-035739 A | 3/2016 |
| JP | 2017-21850 A | 1/2017 |

OTHER PUBLICATIONS

Office Action dated Sep. 26, 2023, in corresponding Japanese Patent Application No. 2019-236252, 4 pages.

* cited by examiner

| Site | Disease | Reference number of cases | |
|---|---|---|---|
| | | Middle ranking | Expert |
| Liver | Liver cirrhosis | 100 cases | 500 cases |
| Pancreas | Pancreatic cancer | 120 cases | 300 cases |
| Liver | Liver cancer | 150 cases | 400 cases |
| ... | ... | ... | ... |

FIG. 3

| Modality | Site | Disease | Reference time | | |
|---|---|---|---|---|---|
| | | | Novice | Middle ranking | Expert |
| CT | Liver | Liver cirrhosis | 30 min | 20 min | 15 min |
| CT | Pancreas | Pancreatic cancer | 40 min | 30 min | 20 min |
| MR | Liver | Liver cancer | 40 min | 30 min | 20 min |
| ... | ... | ... | ... | ... | ... |

FIG. 4

| Radiologist ID | Modality | Site | Disease | Proficiency attainment time | | Weighting |
|---|---|---|---|---|---|---|
| | | | | Middle ranking | Expert | |
| Novice A | CT | Liver | Liver cirrhosis | 2020/3/25 | 2025/3/25 | 1 |
| Novice A | MR | Liver | Liver cancer | 2020/3/25 | 2025/3/25 | 1 |
| Novice B | MR | Liver | Liver cancer | 2020/3/25 | 2025/3/25 | 1 |
| Middle ranking A | CT | Pancreas | Pancreatic cancer | — | 2025/3/25 | 1 |
| Expert A | CT | Liver | Liver cirrhosis | — | — | — |
| ... | ... | ... | ... | ... | ... | ... |

500

F I G. 5

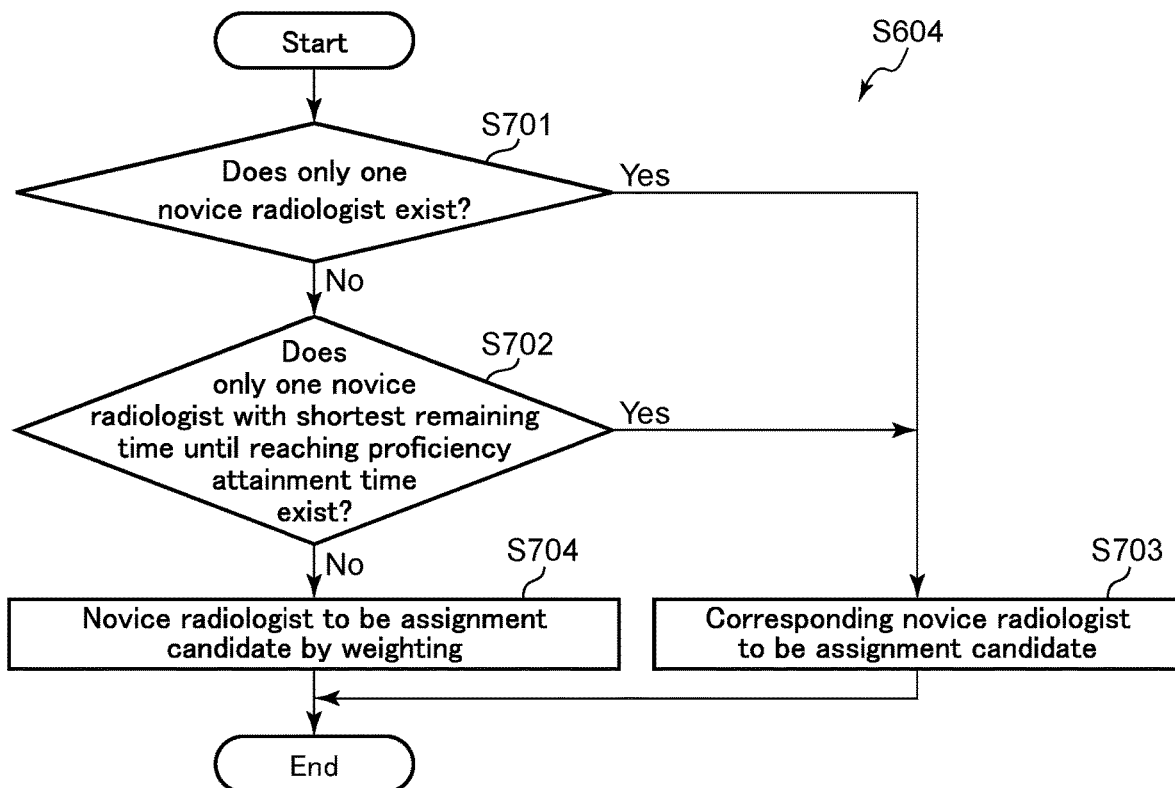
F I G. 7
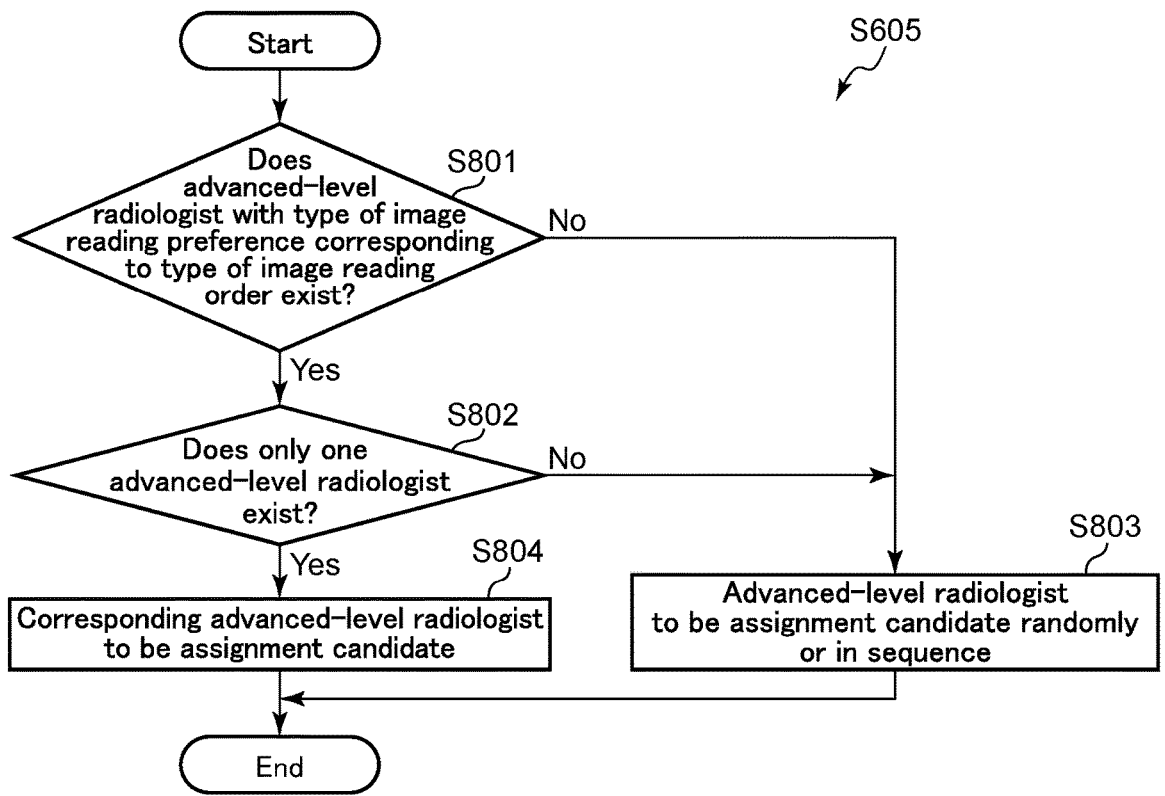
F I G. 8

| Order No. | Modality | Site | Urgency |
|---|---|---|---|
| 1 | CT | Liver | Present |
| 2 | CT | Pancreas | Absent |
| 3 | MR | Liver | Absent |
| ... | ... | ... | ... |

| Task ID | Order No. | Modality | Site | Doctor in charge | Preceding task | Predicted time |
|---|---|---|---|---|---|---|
| 1 | 1 | CT | Liver | Advanced-level A | Null | 20 min |
| 2 | 2 | CT | Pancreas | Advanced-level B | Null | 30 min |
| 3 | 3 | MR | Liver | Novice A | Null | 40 min |
| 4 | 3 | MR | Liver | Advanced-level A | 3 | 20 min |
| ... | ... | ... | ... | ... | ... | ... |

F I G. 11

| Task ID | Order No. | Modality | Site | Disease | Doctor in charge | Preceding task | Implementation time | Approval | Like |
|---|---|---|---|---|---|---|---|---|---|
| 3 | 3 | MR | Liver | Liver cirrhosis | Novice A | Null | 35 min | ☑ | ☑ |
| 4 | 3 | MR | Liver | Liver cirrhosis | Advanced-level A | 3 | 15 min | Null | Null |
| 5 | 4 | MR | Liver | — | Novice B | Null | 10 min | ☐ | ☐ |
| 6 | 4 | MR | Liver | — | Advanced-level A | 5 | 40 min | Null | Null |
| ... | ... | ... | ... | ... | ... | ... | ... | ... | ... |

140

F I G. 14

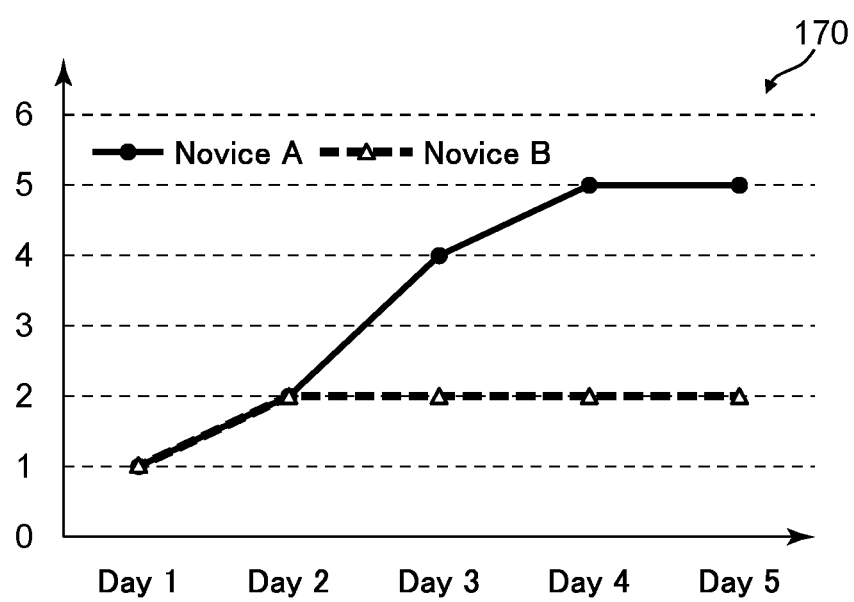
F I G. 17

| Radiologist ID | Modality | Site | Disease | Proficiency attainment time | | Weighting |
| --- | --- | --- | --- | --- | --- | --- |
| | | | | Middle ranking | Expert | |
| Novice A | CT | Liver | Liver cirrhosis | 2020/3/25 | 2025/3/25 | 1.0 |
| Novice A | MR | Liver | Liver cancer | 2020/3/25 | 2025/3/25 | 1.0 |
| Novice B | MR | Liver | Liver cancer | 2100/3/25 | 2100/3/25 | 0.5 |
| Middle ranking A | CT | Pancreas | Pancreatic cancer | — | 2025/3/25 | 1 |
| Expert A | CT | Liver | Liver cirrhosis | — | — | — |
| ⋯ | ⋯ | ⋯ | ⋯ | ⋯ | ⋯ | ⋯ |

FIG. 18

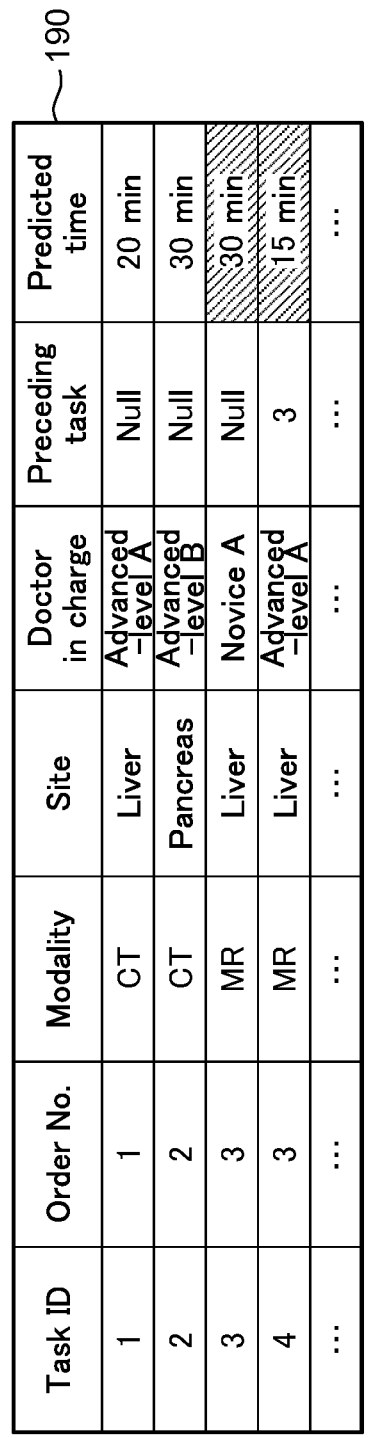
F I G. 19

TASK ASSIGNMENT SUPPORTING APPARATUS, TASK ASSIGNMENT SUPPORTING SYSTEM, AND TASK ASSIGNMENT SUPPORTING METHOD

CROSS-REFERENCE TO RELATED APPLICATIONS

This application is based upon and claims the benefit of priority from the prior Japanese Patent Application No. 2019-236252, filed Dec. 26, 2019, the entire contents of which are incorporated herein by reference.

FIELD

Embodiments described herein relate generally to a task assignment supporting apparatus, a task assignment supporting system, and a task assignment supporting method.

BACKGROUND

In image diagnosing tasks, a clinician who provides medical diagnosis and treatment to a patient issues an examination order to request an examination. A technician confirms the examination order through a radiology information system (RIS) and implements a radiographic examination. Subsequently, a radiologist reads an image obtained by the radiographic examination and prepares an image reading report on a provisional view and diagnosis thereof. The clinician confirms the image reading report, and, after recording a final view and diagnosis along with a treatment strategy thereof on a medical record, explains this to the patient.

For example, in the past, for an image reading task, a radiologist was required to be a generalist who is able to read images of any medical field and of any site on a patient at a hospital. However, nowadays, due to the widespread use of remote image reading, it has become possible to request image reading of radiologists at remote locations who are proficient in image reading of specific fields or sites. Therefore, novice radiologists now wish to have careers specializing in a specific field of study and a specific site. On the other hand, in consideration of a case of emergency or a hospital's policy, there are many cases in which radiologists are nurtured as generalists.

Generally, in most cases, reading tasks to be performed by the radiologists are decided depending on a local rule of each hospital. Therefore, in a case where a plurality of radiologists randomly perform the image reading tasks, novice radiologists may not be able to perform image reading tasks in accordance with a career he/she desires, which may also lead to a possibility of receiving no guidance from an advanced-level radiologist.

BRIEF DESCRIPTION OF THE DRAWINGS

FIG. 3 shows an example of a number of prepared image reading reports table.

FIG. 4 shows an example of a time for preparing image reading report table.

FIG. 5 shows an example of a preferred image reading type table.

FIG. 7 shows an example of assigning processing of a novice radiologist performed by the task assignment supporting apparatus according to the first embodiment.

FIG. 8 shows an example of assigning processing of an advanced-level radiologist performed by the task assignment supporting apparatus according to the first embodiment.

FIG. 11 shows an example of a radiologist assignment table.

FIG. 14 shows an example of a record of image reading implementation table.

FIG. 17 shows an example of a like-evaluation transition.

FIG. 18 shows an example of a revised preferred image reading type table.

FIG. 19 shows an example of a revised radiologist assignment table.

DETAILED DESCRIPTION

Figure 1:
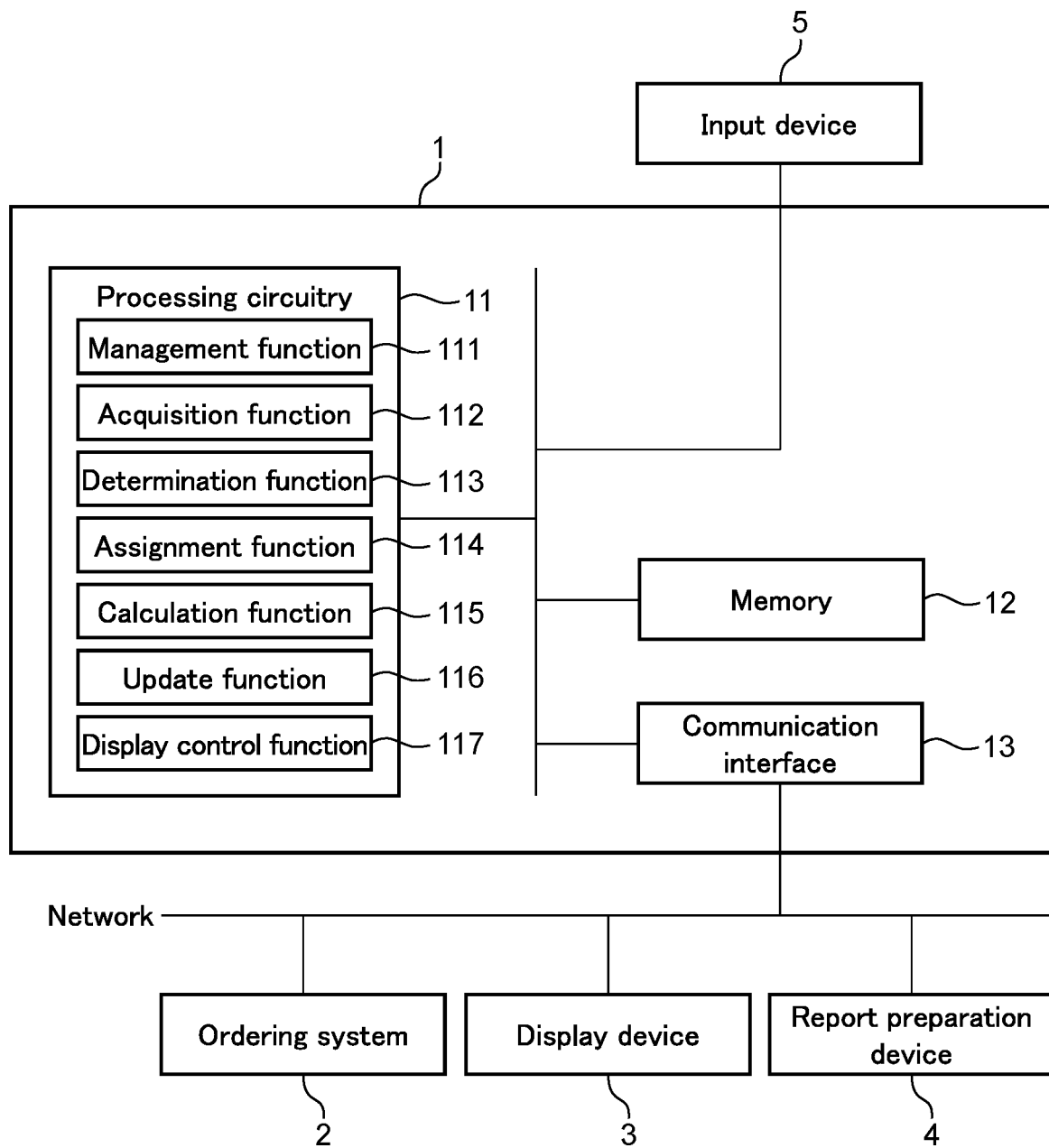
FIG. 1 shows an example of a configuration of a task assignment'supporting apparatus according to a first embodiment.

In general, according to one embodiment, a task assignment supporting apparatus includes processing circuitry. The processing circuitry manages types of image reading preferences indicating types of image reading tasks preferred by each radiologist. The processing circuitry acquires an image reading order and a type of image reading order indicating a type of image reading task required for the image reading order. The processing circuitry assigns to the image reading order a radiologist with a type of image reading preference corresponding to the type of image reading order.

Hereinafter, a task assignment supporting apparatus, a task assignment supporting system, and a task assignment supporting method according to embodiments will be explained with reference to the drawings. In the following embodiments, elements assigned the same reference numerals perform the same operations, and redundant explanations will be omitted as appropriate. Hereinafter, an embodiment will be explained with reference to the drawings.

First Embodiment

An example of a configuration of a task assignment supporting apparatus according to a first embodiment will be explained with reference to FIG. 1. In the following embodiment, a radiologist is assumed to be a doctor, and an image reading task is assumed to be a medical task. Therefore, a task assignment supporting system and a task assignment supporting apparatus in the case of performing processing for an image reading task will be referred to respectively as an image reading task assignment supporting system and an image reading task assignment supporting apparatus. It should be noted that the task assignment supporting apparatus according to the present embodiment is not limited to being used for an image reading task of a radiologist, and may also be used for assigning other medical tasks, such a surgical task of a surgeon or an examination task of a laboratory technician.

The task assignment supporting system shown in FIG. 1 includes a task assignment supporting apparatus 1, an ordering system 2, a display device 3, a report preparation device 4, and an input device 5. The task assignment supporting apparatus 1 is configured by processing circuitry 11, a memory 12, and a communication interface 13. The processing circuitry 11, the memory 12, the communication interface 13, and the input device 5 are, for example, connected to one another via a bus in a communicatory manner. Furthermore, the task assignment supporting apparatus 1 is connected to the ordering system 2, the display device 3, and the report preparation device 4, which are external systems or external devices provided separately from the task assignment supporting apparatus 1, via a network in a communicatory manner. Here, a proxy server may be installed as a device functioning as a firewall between the task assignment supporting apparatus 1 and the external systems or the external devices.

It should be noted that the processing circuitry 11, the memory 12, and the communication interface 13 configuring the task assignment supporting apparatus 1 do not necessarily have to be realized by individual pieces of hardware. For example, at least two of the processing circuitry 11, the memory 12, and the communication interface 13 may coexist in one piece of hardware.

The processing circuitry 11 takes total control over the task assignment supporting apparatus 1 according to electrical signals of input operations output from the input device 5. For example, the processing circuitry 11 includes, as hardware resources, a processor such as a CPU or a GPU. By executing a program developed on the memory 12 via the processor, the processing circuitry 11 realizes each function (a management function 111, an acquisition function 112, a determination function 113, an assignment function 114, a calculation function 115, an update function 116, and a display control function 117). It should be noted that each of the functions is not limited to being realized by processing circuitry with a single processor. For example, the processing circuitry may be configured by combining a plurality of independent processors, and each of the functions may be realized by each of the processors executing the program.

The management function 111 manages various kinds of information. For example, the management function 111 manages types of image reading preferences indicating types of image reading tasks preferred by each radiologist. The types of image reading preferences will be described later in FIG. 5.

The acquisition function 112 acquires various kinds of information. For example, the acquisition function 112 acquires image reading orders and types of image reading orders indicating types of image reading tasks preferred for the image reading orders. The types of image reading orders will be described later in FIG. 9.

The determination function 113 performs calculation processing by using various kinds of information to determine whether or not various conditions are being satisfied.

The assignment function 114 assigns various targets to various assignment destinations. For example, to the image reading order, the assignment function 114 assigns a radiologist with the type of the image reading preference that corresponds to the type of the image reading order. Furthermore, after assigning a first radiologist, the assignment function 114 assigns a second radiologist with a higher proficiency than the first radiologist to the image reading order.

The calculation function 115 performs various calculations. For example, the calculation function 115 calculates a work cost relating to the radiologist. The calculation function 115 also calculates work costs relating to a first doctor and a second doctor, respectively. The work costs will be described later in FIG. 6 and FIG. 10.

The update function 116 updates and stores various kinds of information. For example, the update function 116 successively updates and stores values input to various diagrams.

The display control function 117 controls various screen displays. For example, the display control function 117 displays various diagrams on the display device 3.

The memory 12 stores various kinds of information. For example, the memory 12 includes a semiconductor memory device such as a random access memory (RAM) as hardware resources. The memory 12 may also be a driving device that reads and writes information to and from external storage devices, such as a hard disk, an optical disk (a CD, a DVD, a Blu-ray (registered trademark), and an Ultra HD Blu-ray (registered trademark)), a flash memory (a USB flash memory, a memory card, and an SSD), and a magnetic tape. Furthermore, a storage region of the memory 12 may be the task assignment supporting apparatus 1 or may be the external storage device.

The communication interface 13 transmits and receives information between the ordering system 2, the display device 3, and the report preparation device 4 in a wired or a wireless manner. Any communication standard can be used between the communication interface 13 and the external systems and the external devices. For example, health level 7 (HL7) can be used for communications relating to medical care information, and Digital Imaging and Communications in Medicine (DICOM) can be used for communications relating to medical image information, as appropriate.

The ordering system 2 receives and manages various medical care orders. For example, the ordering system 2 manages an image reading order relating to image reading.

The display device 3 displays various kinds of information. As the display device 3, any display such as a cathode ray tube (CRT) display, a liquid crystal display (LCD), a plasma display, an organic electro-luminescence display (OELD), and a tablet terminal can be used.

The report preparation device 4 is a computer on which software for preparing an image reading report is mounted. For example, the report preparation device 4 outputs an implementation time required for preparing the image reading report to the task assignment supporting apparatus 1.

The input device 5 receives various inputs from an operator and converts the received inputs into electrical signals to output to the task assignment supporting apparatus 1. As the input device 5, for example, physically operated parts such as a mouse, a keyboard, a trackball, a switch, a button, a joystick, a touch pad, or a touch panel display can be used. It should be noted that a GUI and a CUI can be used as the types of input device 5.

Figure 2:
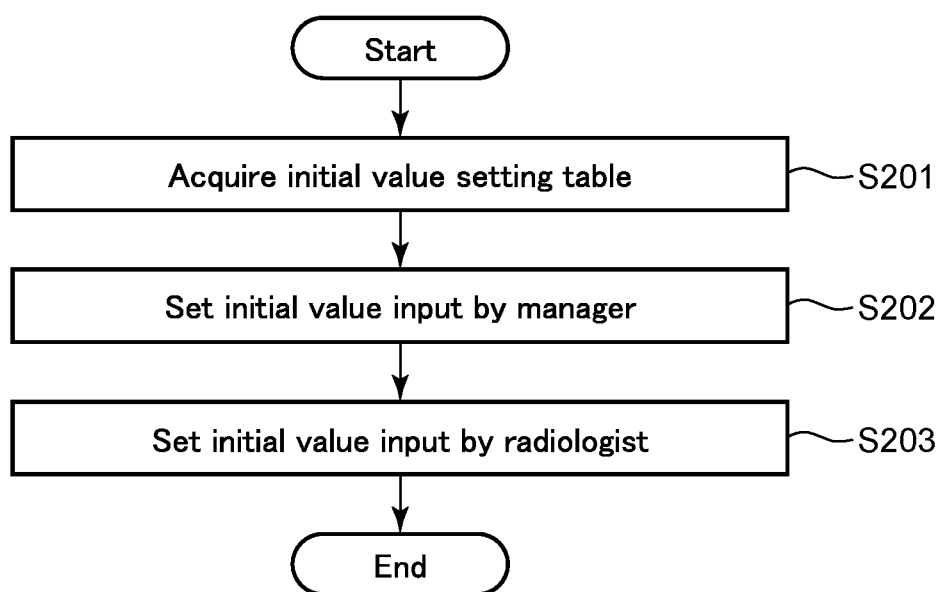
FIG. 2 shows an example of a preparation operation of the task assignment supporting apparatus according to the first embodiment.

An example of a preparation operation of the task assignment supporting apparatus 1 according to the first embodiment will be explained with reference to FIG. 2. In the following embodiment, radiologists are classified into one of the three levels (novice, middle ranking, and expert) in accordance with their proficiency relating to the image reading task. Furthermore, a novice radiologist (an example of a first doctor) indicates a radiologist who does not have much experience in the image reading task, and an advanced-level radiologist (an example of a second doctor) indicates a radiologist who has more experience than the novice radiologist and has a higher proficiency than the novice radiologist. The advanced-level radiologist is, for example, a middle ranking or an expert level radiologist.

In step S201, the acquisition function 112 acquires an initial value setting table that is stored in the memory 12. The initial value setting table indicates a number of prepared image reading reports table 300, a time for preparing image reading report table 400, and a preferred image reading type table 500. An example of each table will be described later with reference to FIG. 3 to FIG. 5.

Here, the acquired initial value setting table is displayed on the display device 3 by the display control function 117. The number of prepared image reading reports table 300, the time for preparing image reading report table 400, and the preferred image reading type table 500 are displayed on the display device 3. A user using the task assignment supporting apparatus 1 inputs a value to a cell of each table that accepts input via the input device 5. The cell that accepts input includes, for example, a cell configuring a table body of each table. The input value is updated and stored successively by the update function 116. Each table may be displayed by switching tabs or may be displayed in parallel on the same display device 3. Furthermore, the input value may be selected from a pull-down list set to the cell.

In step S202, the management function 111 sets initial values to cells of the number of prepared image reading reports table 300 and the time for preparing image reading report table 400 that accept input. Here, for example, the initial value is set by receiving an input from a manager using the task assignment supporting apparatus 1. For example, the manager includes medical professionals who are different from radiologists. A password may be set for each of the number of prepared image reading reports table 300 and the time for preparing image reading report table 400 to limit browsing and editing so that the tables can only be confirmed and changed by the manager.

In step S203, the management function 111 sets an initial value to a cell of the preferred image reading type table 500 that accepts input. Here, for example, the initial value is set by receiving an input from a radiologist, including a novice radiologist and an advanced-level radiologist. In the preferred image reading type table 500, for example, the initial value may be input by any method, such as, by each of the radiologists.

It should be noted that, in the above-mentioned preparation operation, an example of the manager and the radiologist inputting the initial value via the input device 5 to a blank input initial value setting table stored in the memory 12 is explained. However, it is not limited thereto. For example, an initial value setting table input by the manager and the radiologist respectively using their own computers may be acquired by the task assignment supporting apparatus 1 via the communication interface 13. Furthermore, the order in which the initial value is input may be the radiologist, then the manager.

An example of the initial value setting table will be explained with reference to FIG. 3 to FIG. 5.

Hereinafter, items relating to each table will be explained. A "radiologist ID" indicates a management number for uniquely identifying radiologists. In the present embodiment, the radiologist ID is expressed by (proficiency)+(one letter) for the sake of convenience. However, it is not limited thereto. A "modality" indicates the type of medical image diagnostic device that has acquired a medical image to be read. In the present embodiment, for the sake of convenience, the modality is assumed to be the type of medical image to be read. The modality includes, for example, a simple X-ray image (X-ray), an X-ray CT image (CT), an MR image (MR), a nuclear medicine image (RI), and an ultrasound image (UL). A "site" indicates an anatomical site of a patient to be read. The anatomical site includes organs such as a brain, a lung, a heart, a liver, a pancreas, a stomach, a small intestine, and a large intestine. A "disease" indicates the type of disease that exists on the "site" to be read. For example, the type of the disease existing on the "liver" may be liver cirrhosis, liver cancer, or hepatitis.

Each table is stored in the memory 12 as table data prepared in a text file format of, for example, a text format (txt), a tab delimited file format (tsv), and a comma delimited file format (csv). The items relating to each table may be in any order.

FIG. 3 shows an example of the number of prepared image reading reports table 300 indicating the number of prepared image reading reports, that is, the reference number of cases necessary for a novice radiologist to become a middle ranking or an expert level radiologist. A "reference number of cases" is a reference value that is to be a reference of the number of image readings relating to the image reading order, and is set according to the proficiency of the radiologist. The number of prepared image reading reports table 300 stores the "site" and the "disease" of the patient shown in the image to be read as well as the reference number of cases of the "middle ranking" and the "expert" in an associated manner. Here, for the sake of convenience in explanation, a predetermined value is input to a cell that accepts input. Hereinafter, unless explained otherwise, it is similarly assumed that a predetermined value is input to a cell that accepts input for each table that is explained.

It should be noted that, in the number of prepared image reading reports table 300, although the number of prepared image reading reports can be input according to the site and the disease, it is not limited thereto. For example, the number of prepared image reading reports necessary for each of the middle ranking level and the expert level may be input without distinguishing the site and the disease. Alternatively, the number of prepared image reading reports may be distinguished by the site or the disease and input. Furthermore, the reference number of cases may be managed in association with each of the radiologists instead of by the proficiency of the radiologist.

For example, in the first row of the entry of the number of prepared image reading reports table 300, a site "liver", a disease "liver cirrhosis", and a reference number of cases "middle ranking" "100 cases" and "expert" "500 cases" are stored in an associated manner.

FIG. 4 shows an example of the time for preparing image reading report table 400 indicating a standard time, that is, a reference time, for a radiologist in each level of novice, middle ranking, and expert to prepare the image reading report. A "reference time" is a reference value that is to be a reference of the image reading time relating to the image reading order, and is set according to the proficiency of the radiologist. The time for preparing image reading report table 400 stores the "modality", the "site", the "disease", and the reference time of "novice", "middle ranking", and "expert" in an associated manner.

It should be noted that, in the time for preparing image reading report table 400, the image reading report preparation time may be further segmented in accordance with a "stage" of the "disease". The "stage" corresponds to the purpose of the image reading. For example, if the image reading is performed to specify a disease, the "stage" will be "confirm nature of disease", and, if the image reading is related to a prognosis of a disease, the stage will be "progress observation". That is, even when the image reading is performed with respect to the same disease, the image reading report preparation time may be set in accordance with the image reading purpose. Furthermore, the reference time may be managed in association with each of the radiologists instead of by the proficiency of the radiologist.

For example, in the first row of the entry of the time for preparing image reading report table 400, modality "CT", site "liver", disease "liver cirrhosis", and reference time "novice" "30 min", "middle ranking" "20 min", and "expert" "15 min" are stored in an associated manner.

FIG. 5 shows an example of the preferred image reading type table 500 indicating types of image reading tasks preferred by the radiologist. The preferred image reading type table 500 stores the radiologist and the type of image reading preference in an associated manner. Specifically, the preferred image reading type table 500 stores the radiologist ID, the modality, the site, the disease, a proficiency attainment time, and weighting. The "proficiency attainment time" indicates a time for a radiologist to attain proficiency, and is set according to the proficiency of the radiologist. In the present embodiment, a date on which each of the radiologists would attain proficiency is set as the proficiency attainment time. The "weighting" is weighting used when determining an assignment ratio of the number of image reading orders for the radiologist. For example, in a case where there are a plurality of radiologists corresponding to the same image reading order attribute, a radiologist to whom a higher weighting is set will be prioritized and assigned to the image reading order. The proficiency attainment time may be calculated based on at least one of the number of image readings per unit term, the reference value of the number of image readings, or the weighting.

For example, in the first row of the entry of the preferred image reading type table 500, radiologist ID "novice A", modality "CT", site "liver", disease "liver cirrhosis", proficiency attainment time "middle ranking" "2020/3/25" and "expert" "2025/3/25", and weighting "1" are stored in an associated manner.

An example of the operation of the task assignment supporting apparatus according to the first embodiment will be explained with reference to FIG. 6.

In step S601, the acquisition function 112 acquires an image reading order list 900 from the ordering system 2 via the communication interface 13. An example of the image reading order list 900 will be described later in FIG. 9.

In step S602, the determination function 113 reads out an image reading order described on the image reading order list 900 and determines whether or not there is urgency. Here, the sequence and the number of image reading orders to be read out may be set freely. For example, if information indicating that the order is urgent is added thereto, it is determined that the image reading order is urgent.

Here, for an image reading order that is determined to be urgent, the operation proceeds to step S605. On the other hand, for an image reading order that is determined not to be urgent, the operation proceeds to step S603.

In step S603, the determination function 113 determines whether or not there is a novice radiologist whose type of image reading preference corresponds to the type of image reading order included in the image reading order. Specifically, it is determined whether or not the "modality" and the "site" of the image reading order described in the image reading order list 900 are a match with the "modality" and the "site" of one of the novice radiologists described in the preferred image reading type table 500.

Here, for an image reading order that is determined to have a novice radiologist with the type of image reading preference corresponding to the type of image reading order included in the image reading order, the operation proceeds to step S604. On the other hand, for an image reading order that is determined to not have such a novice radiologist, the operation proceeds to step S605.

In step S604, a novice radiologist who is to be an assignment candidate of the image reading order is determined. Detailed processing will be described later in FIG. 7.

In step S605, an advanced-level radiologist who is to be the assignment candidate of the image reading order is determined. Here, as for the image reading order that is determined to not be urgent in step S602, subsequent to determining a novice radiologist who is to be the assignment candidate in step S604, an advanced-level radiologist to confirm and check the image reading report prepared by the novice radiologist is determined. On the other hand, for the image reading order that is determined to be urgent in step S602, without determining a novice radiologist for the assignment candidate, only an advanced-level radiologist is determined for the assignment candidate. Detailed processing will be described later in FIG. 8.

In step S606, the determination function 113 determines whether or not all of the image reading orders described in the image reading order list 900 are processed.

Here, in the case where all of the image reading orders are processed, the operation proceeds to step S608. On the other hand, in the case where there are image reading orders yet to be processed, the operation proceeds to step S607.

In step S607, the acquisition function 112 acquires the next image reading order for which assignment candidates are to be determined. For example, in a case where a radiologist who is to be the assignment candidate has already been set for the image reading order relating to the first row of the image reading order list 900, an image reading order is acquired in relation to the second row of the entry. After the acquirement, the operation returns to step S602.

In step S608, the calculation function 115 calculates the estimated work cost relating to each radiologist in the case of assigning the radiologists to each of the image reading orders in the image reading order list 900. The work cost indicates a task load received by the radiologist. In the present embodiment, the work cost includes, for example, a time predicted to be necessary for the image reading, that is, a predicted time. For the calculation of the work cost, a reference time in the time for preparing image reading report table 400 at which the "modality" and the "site" of the image reading order and the proficiency (novice, middle ranking, expert) of the radiologist who is to be the assignment candidate match should be used. Here, in a case where the "disease" in the image to be read is determined in the image reading order, an input value taking into account whether or not the "disease" in the time for preparing image reading report table 400 is also a match may also be used.

The calculation result may also be displayed as an estimated work cost 100 using a graph. An example of the estimated work cost 100 will be described later in FIG. 10.

In step S609, the determination function 113 determines whether or not there is a radiologist who exceeds the upper limit value of the work cost.

Here, in a case where it is determined that a radiologist who exceeds the upper limit value of the work cost exists, the operation proceeds to step S610. On the other hand, in a case where it is determined that such a radiologist does not exist, the operation proceeds to step S611.

In step S610, for a part of the image reading order assigned to a radiologist who exceeds the upper limit value of the work cost, the assignment function 114 redetermines another radiologist who would not exceed the upper limit value of the work cost when the part of the image reading order is assigned thereto, as the assignment candidate. When redetermining the radiologist, a radiologist having a type of image reading preference that does not correspond to the type of image reading order in the image reading order may be assigned. That is, the assignment should be made in a manner not to exceed the upper limit value of the work cost for each radiologist. After the radiologist is redetermined, the operation proceeds to step S611.

In step S611, the assignment function 114 assigns the radiologist in accordance with the assignment candidate determined for each image reading order. The assignment result shows tasks to be performed by each radiologist, and is displayed by a diagram such a radiologist assignment table 110. An example of the radiologist assignment table 110 will be described later in FIG. 11.

Subsequently, details of the assignment processing of a novice radiologist relating to step S604 shown in FIG. 6 will be explained with reference to FIG. 7.

In step S701, the determination function 113 determines whether or not there is only one novice radiologist with the type of image reading preference corresponding to the type of image reading order included in the image reading order.

Here, in the case where there is only one novice radiologist as such, the processing proceeds to step S703. On the other hand, in the case where there are a plurality of novice radiologists, the processing proceeds to step S702.

In step S702, the determination function 113 determines whether or not there is only one novice radiologist who has the shortest remaining period between the current point and the proficiency attainment time among the plurality of novice radiologists who are contenders to be the assignment candidate.

Here, in the case where there is only one novice radiologist as such, the processing proceeds to step S703. On the other hand, in the case where there are a plurality of such novice radiologists, the processing proceeds to step S704.

In step S703, the assignment function 114 assigns the only novice radiologist determined in the determination processing of step S701 or step S702 as the assignment candidate.

In step S704, the assignment function 114 selects one novice radiologist as an assignment candidate from among the plurality of novice radiologists who are contenders to be the assignment candidate. Here, the "weighting" in the preferred image reading type table 500 is used to determine the assignment candidate. For example, if the weighting is an actual value, the weighting set in accordance with the type of image reading preference of the radiologist may be assigned as the assignment ratio. For example, in a case where the weighting of a certain novice radiologist A is "2", and the weighting of another novice radiologist B is "1", the novice radiologists are assigned randomly or in sequence by the assignment ratio of novice radiologist A:novice radiologist B=2:1.

It should be noted that the weighting may be a value set relatively among novice radiologists, or may be a value set relatively among a plurality of types of image reading preferences of one novice radiologist. For example, in a case where one novice radiologist wishes to read both a CT image and an MR image when reading a liver, and wishes to prioritize reading the MR image, the weighting may be set to CT image: MR image=1:2.

Subsequently, details of the assignment processing of an advanced-level radiologist relating to step S605 shown in FIG. 6 will be explained with reference to FIG. 8. Basically, the assignment processing is pursuant to that of the novice radiologist.

In step S801, the determination function 113 determines whether or not there is an advanced-level radiologist with the type of image reading preference corresponding to the type of image reading order included in the image reading order.

Here, for the image reading order of which an advanced-level radiologist is determined to exist, the processing proceeds to step S802. On the other hand, for the image reading order of which such an advanced-level radiologist is determined not to exist, the processing proceeds to step S803.

In step S802, the determination function 113 determines whether or not there is only one advanced-level radiologist with the type of image reading preference corresponding to the type of image reading order of the image reading order.

Here, in the case where there is only one advanced-level radiologist as such, the processing proceeds to step S804. On the other hand, in the case where there are a plurality of advanced-level radiologists, the processing proceeds to step S803.

In step S803, the assignment function 114 selects one advanced-level radiologist as an assignment candidate from among the plurality of advanced-level radiologists who are contenders to be the assignment candidate. Here, one advanced-level radiologist should be assigned randomly or in sequence from among the plurality of advanced-level radiologists.

In step S804, the assignment function 114 assigns the only advanced-level radiologist determined in the determination processing of step S802 as the assignment candidate.

Figure 6:
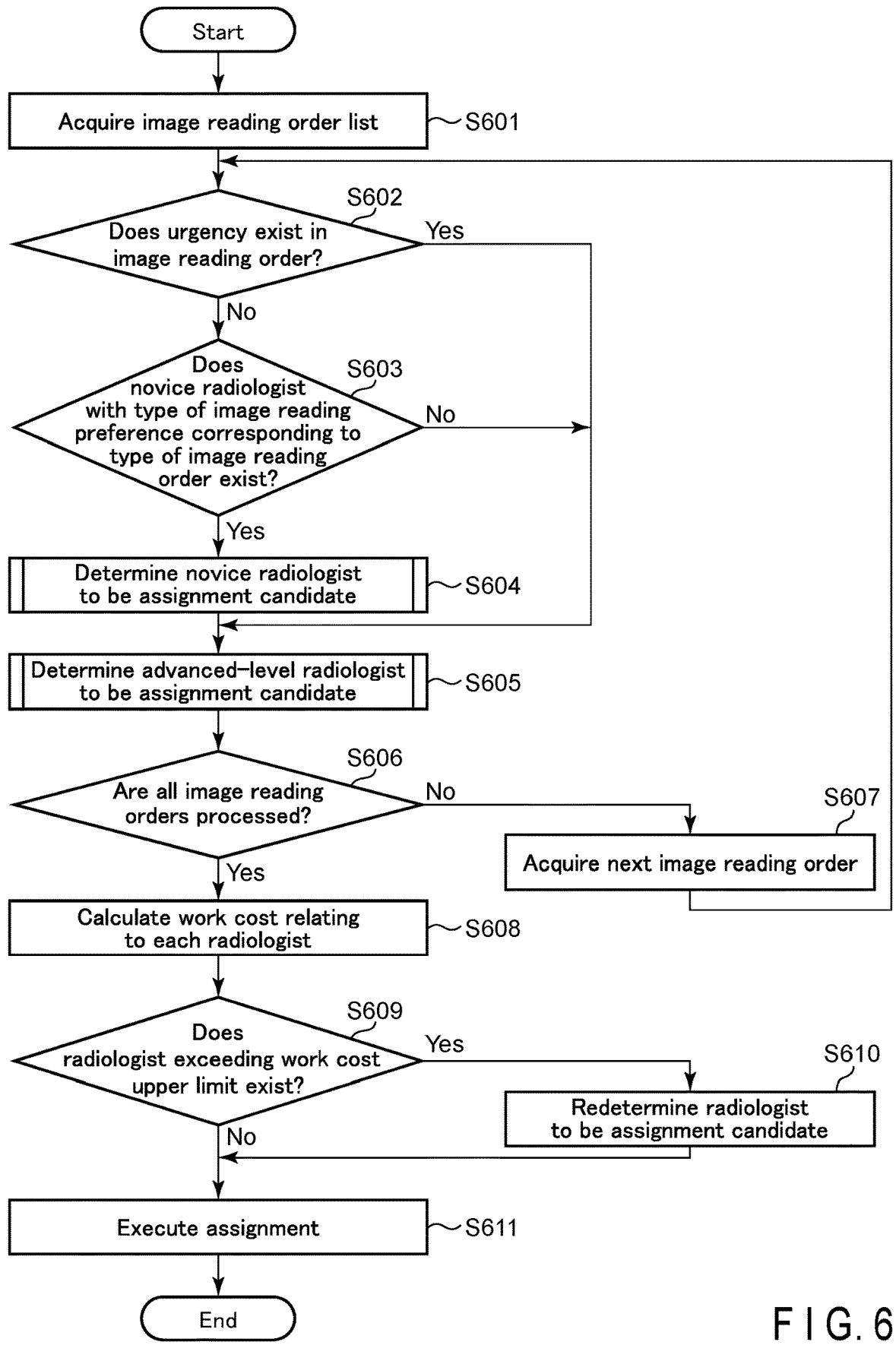
FIG. 6 shows an example of an operation of the task assignment supporting apparatus according to the first embodiment.

In FIG. 6 to FIG. 8, an example of assigning an advanced-level radiologist after assigning a novice radiologist to the image reading order is explained. However, it is not limited thereto. For example, the image reading order may be assigned to all of the radiologists without distinguishing novice radiologists from the advanced-level radiologists. That is, with reference to the preferred image reading type table 500, a radiologist with the type of image reading preference corresponding to the type of image reading order of a certain image reading order may be assigned to the image reading order. When doing so, the assignment function 114 should perform the assignment so that a work cost of the radiologist calculated based on a reference value of the image reading time does not exceed a threshold value.

Furthermore, the assignment function 114 may change the assignment ratio of the number of image reading orders in accordance with the remaining number of image readings until the reference value of the number of image readings is reached when assigning a plurality of image reading orders to a plurality of radiologists. For example, the assignment ratio may be changed so that a radiologist with the largest remaining number of image readings until the reference value is reached is prioritized to be assigned the image reading order among the plurality of radiologists.

Furthermore, the assignment function 114 may change the assignment ratio of the number of image reading orders in accordance with the weighting in the preferred image reading type table 500 when assigning a plurality of image reading orders to a plurality of radiologists. That is, the assignment ratio may be changed so that a radiologist with a large weighting is prioritized to be assigned the image reading order among the plurality of radiologists. Furthermore, the assignment function 114 may change the assignment ratio of the number of image reading orders in accordance with the remaining period until the proficiency attainment time is reached when assigning a plurality of image reading orders to a plurality of radiologists. For example, a radiologist with the shortest remaining period until the proficiency attainment time is reached may be prioritized to be assigned the image reading order among the plurality of radiologists.

An example of the operation of the task assignment supporting apparatus according to the first embodiment will be explained with reference to FIG. 9 to FIG. 11.

Figures 9, 10:
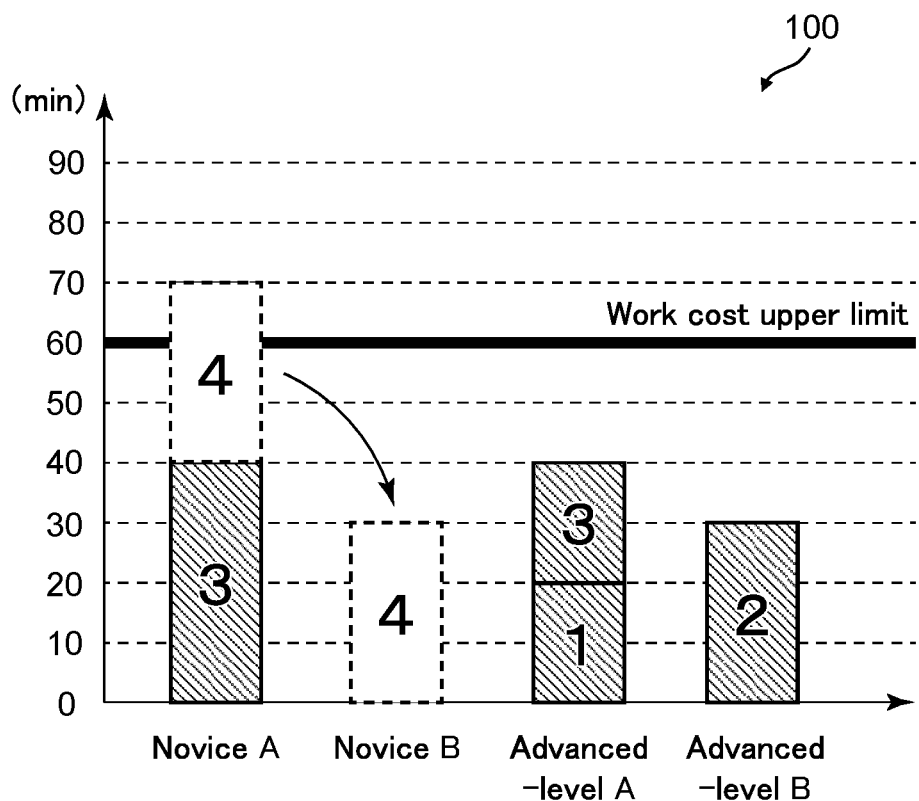
FIG. 9 shows an example of an image reading order list.
FIG. 10 shows an example of an estimated task cost.

FIG. 9 shows an example of the image reading order list 900 indicating a list of image reading orders that are not read. In the image reading order list 900, an "order number" that is a management number of the image reading order, a "modality" indicating the type of medical image diagnostic device acquiring original data of an image to be read, a "site" of a patient shown in the image to be read, and an "urgency" of the image reading order are stored in an associated manner. It should be noted that the image reading order list 900 should describe a list of image reading orders of any day, plurality of days, or period. Here, the combination of the modality and the site is to be the type of image reading order. The type of image reading order may also be a combination of the modality, the site, and the disease.

The urgency is to be set when the image reading order is issued. For example, a client requesting the image reading may set information relating to the urgency to the image reading order, or a clinician may set information relating to the urgency to an examination order to have information relating to the urgency also set to an image reading order associated with the examination order. The mode of describing the urgency is not limited to "present" or "absent", and may be any mode as long as the presence/absence of urgency is expressed in a binary manner, such as by "YES" or "NO" or "1" or "0".

For example, in the first row of the entry of the image reading order list 900, order number "1", modality "CT", site "liver", and urgency "present" are stored in an associated manner.

FIG. 10 shows an example of the estimated work cost 100 indicating a work cost relating to each radiologist estimated in the case of assigning a radiologist who is to be an assignment candidate for each image reading order. In the estimated work cost 100, a horizontal axis indicates a radiologist ID, a vertical axis indicates a work cost, and the work cost is expressed by a stacked bar graph. Furthermore, an upper limit of the work cost is shown by a solid line. Here, the case of assigning the three cases of image reading orders described in the image reading order list 900 to respective radiologists is shown. The number on the bar graph indicates the order number of the assigned image reading order. That is, any display method may be used as long as the corresponding relationship between the radiologist and the work cost relating to the radiologist is explicitly described.

For example, according to the estimated work cost 100, image reading order "3" is assigned to "novice A" indicating a novice radiologist. On the other hand, image reading orders "1" and "3" are assigned to "advanced-level A" indicating an advanced-level radiologist. In this manner, to prevent the work cost of the assigned image reading order from reaching the upper limit value, for example, the image reading order is assigned to each radiologist.

Here, a case is assumed in which an assignment candidate of a new image reading order "4" (a broken line site in FIG. 4) is "novice A", and the work cost of novice A exceeds the upper limit value when and the image reading order "4" is assigned. In this case, the assignment should be made to, for example, "novice B", indicating a different novice radiologist from novice A as a radiologist whose work cost would not exceed the upper limit value even if the image reading order "4" were assigned.

FIG. 11 shows an example of the radiologist assignment table 110 indicating the result of assigning a radiologist to each image reading order. In the radiologist assignment table 110, a "task ID" which is a management number for uniquely identifying a task, an "order number" which is a management number of an image reading order, a "modality" indicating the type of medical image diagnostic device acquiring original data of an image to be read, a "site" of a patient shown in an image to be read, a "doctor in charge" who is in charge of the image reading, a "preceding task" indicating whether or not the image reading is performed with respect to a same image, and a "predicted time" required for the image reading and corresponding to a work cost are stored in an associated manner.

For example, in the first row of the entry of the radiologist assignment table 110, task ID "1", order number "1", modality "CT", site "liver", doctor in charge "advanced-level A", preceding task "Null", and predicted time "20 min" are stored in an associated manner.

Hereinafter, other modifications of the task assignment supporting apparatus 1 according to the present embodiment will be explained.

In the initial value setting table, it may be determined whether or not a certain condition is satisfied for an input numerical value. For example, in the number of prepared image reading reports table 300, the determination function 113 may determine whether or not (numerical value relating to middle ranking) ☐(numerical value relating to expert) is established. If it is not established, a notification such as "value invalid" may be issued to encourage the manager to change the input value, or the system may be set to refuse input of such an input value. Here, (numerical value relating to expert) is assumed to be a numerical value added to the number of prepared image reading reports prepared by a novice radiologist until he/she reaches middle ranking.

In the preferred image reading type table 500, an example of a radiologist manually inputting a voluntary value as the proficiency attainment time has been described. However, it is not limited thereto. For example, the calculation function 115 may calculate the proficiency attainment time and input the value automatically. Here, the calculation formula of the proficiency attainment time may be obtained by the following mathematical expression in a case where, for example, the number of weeks from the current point to the proficiency attainment time is calculated.

$$L = A/(B \times C \times D) + \alpha \tag{1}$$

In the above mathematical expression (1), L indicates the number of weeks from the current point to the proficiency attainment time, A indicates the number of prepared image reading reports in accordance with the proficiency, B indicates the number of attendances per week, C indicates the number of image reading preferences per day, D indicates weighting, and a indicates a margin. Here, for A, the reference number of cases in the number of prepared image reading reports table 300 should be used, and, for D, the weighting in the preferred image reading type table 500 should be used.

Furthermore, based on the proficiency attainment time calculated in the manner above, it may be determined whether or not the manually input proficiency attainment time can be achieved. For example, in a case where the radiologist has input a shorter proficiency attainment time than the calculated proficiency attainment time, a notification such as "value invalid" may be issued to encourage the manager to change the input value, or the system may be set to refuse input of such an input value.

Furthermore, in the estimated work cost 100, in a case where the work cost exceeds the upper limit value, notification such as "word cost exceeded" may be displayed to call the manager's attention. Here, the image reading order may be assigned manually. Furthermore, in a case where a radiologist who does not correspond to the type of image reading preference becomes an assignment candidate, a notification such as "confirm executing assignment?" may be displayed to encourage the manager to confirm the assignment.

Furthermore, an example of assigning an advanced-level radiologist after assigning a novice radiologist to the image reading order has been explained. However, it is not limited thereto: For example, in a case where all of the image reading orders received in the morning are to be checked by one advanced-level radiologist, the advanced-level radiologist who is to be the checker may be assigned to a plurality of image reading orders prior to the novice radiologist. Subsequently, the image reading orders may be assigned to the novice radiologist who performs the image reading task. In such a case, in the radiologist assignment table 110, the task ID may be blank at a stage where the advanced-level radiologist is assigned to the image reading order. The task ID of the advanced-level radiologist may be updated to refer to the task ID of the novice radiologist after the novice radiologist is assigned.

In the above, the image reading task assignment method has been explained as an example of assigning a task to be executed by the task assignment supporting apparatus 1. However, the method is not limited thereto, and can be applied even in a case where a task is performed by cooperation between an inexperienced doctor and an experienced doctor. For example, the method can be applied to the assignment of a novice clinician and an advanced-level clinician when the advanced-level clinician is to confirm and check an electronic medical record prepared by the novice clinician.

According to the first embodiment mentioned above, by prioritizing the assignment of a medical care order to a novice doctor in accordance with the type of image reading preference of the novice doctor, the medical care order can be assigned by prioritizing a policy to nurture novice doctors. Furthermore, considering the types of image reading preferences, medical care tasks relating to fields and sites, etc. in which the novice doctors excel can be implemented in a prioritized manner, thereby enabling a specialist in a specific specialized field and site to be nurtured, etc., and enabling novice doctors to be nurtured suitably in accordance with a hospital policy. Furthermore, by assigning tasks actively to novice doctors, task loads on advanced-level doctors may be reduced, thereby enabling suitable task assignments to be implemented.

Second Embodiment

In the task assignment supporting apparatus according to the first embodiment, an operation of prioritizing the image reading order to be assigned in accordance with the type of image reading preference of a novice radiologist is performed. On the other hand, in a task assignment supporting apparatus according to a second embodiment, an operation to confirm and change characteristics and nurturing policies of a novice radiologist is performed based on a quality and a preparation time of an image reading report prepared by the novice radiologist and a checking time of an advanced-level radiologist.

Figure 12:
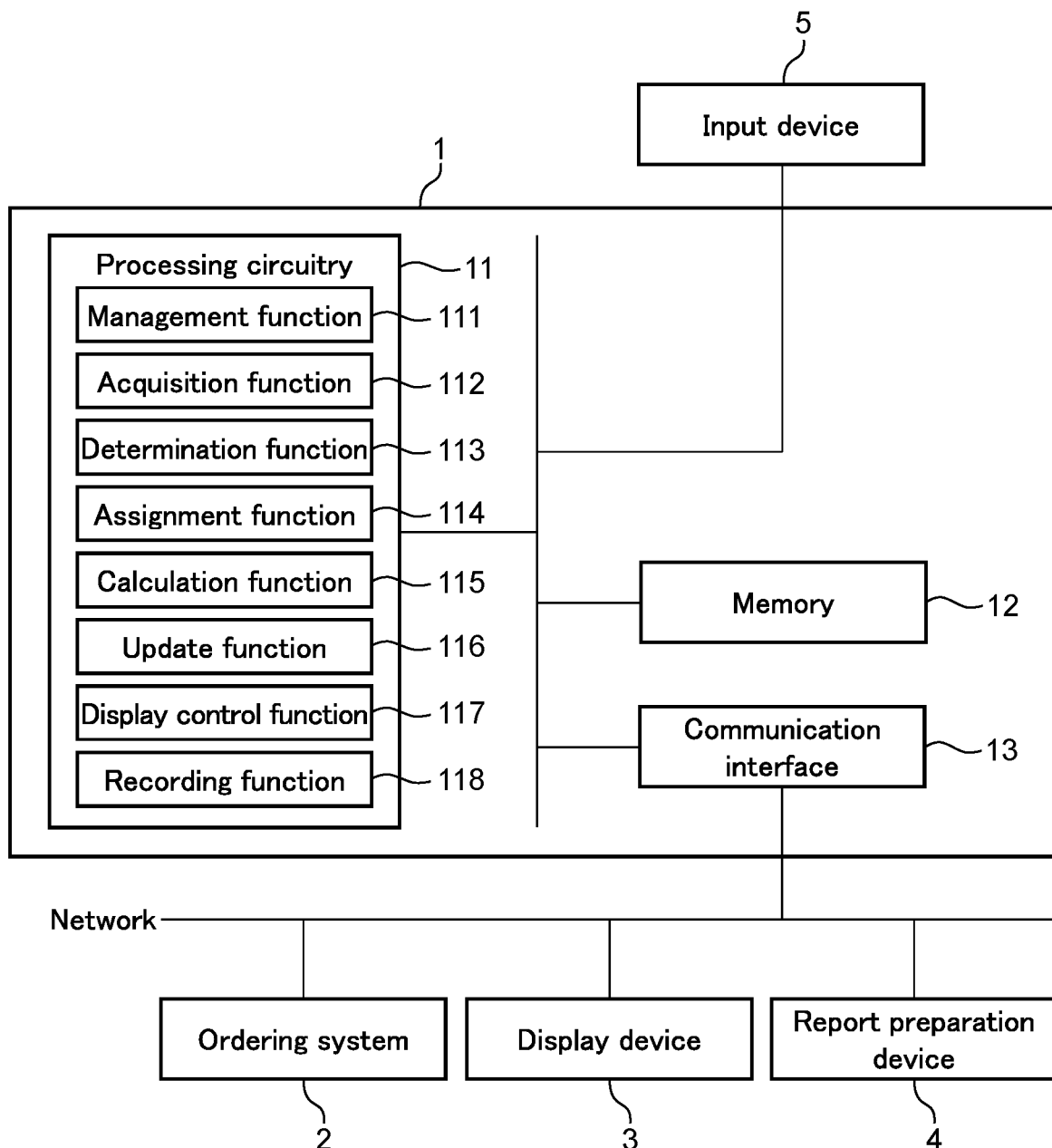
FIG. 12 shows an example of a configuration of a task assignment supporting apparatus according to a second embodiment.

An example of a configuration of the task assignment supporting apparatus according to the second embodiment will be explained with reference to FIG. 12. In the second embodiment, in addition to the configuration described in the first embodiment, a recording function 118 is added to processing circuitry 11.

The recording function 118 records various kinds of information. The recording function 118 records, for example, an implementation time required for an image reading task and evaluations with respect to a processing result of an image reading order.

Figure 13:
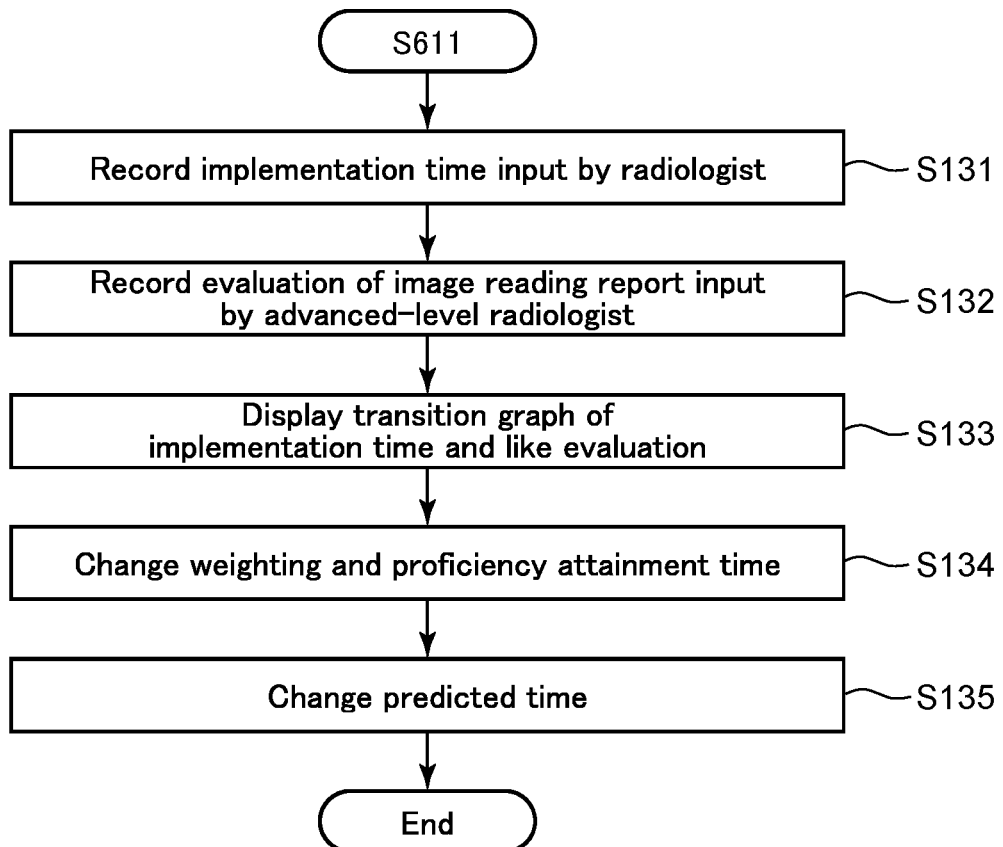
FIG. 13 shows an example of an operation of the task assignment supporting apparatus according to the second embodiment.

An example of the operation of the task assignment supporting apparatus according to the second embodiment will be explained with reference to FIG. 13. In the present operation example, the processing from step S601 to step S611 is executed, and only the processing unique to the present embodiment that is continuous to step S611, will be described.

In step S131, the recording function 118 records the implementation time with respect to a cell of a record of image reading implementation table 140 that accepts input. Here, the implementation time is recorded by receiving input from a radiologist. For example, in the case of a novice radiologist, a time required for preparing an image reading report is input, and, in the case of an advanced-level radiologist, a time required for confirming and checking the image reading report is input. The recording function 118 may also record the implementation time by automatically determining the implementation time from an implementation time, etc. of image reading software of a report preparation device 4. An example of the record of image reading implementation table 140 will be described later in FIG. 14.

In step S132, the recording function 118 records the evaluations of the image reading report with respect to a cell of the record of image reading implementation table 140 that accepts input. Here, the evaluations of the image reading report are recorded by receiving input from an advanced-level radiologist. Specifically, the advanced-level radiologist inputs evaluations with respect to the image reading report of a novice radiologist in charge. Evaluation items include "approval" indicating that the report is approved as an image reading report, and an evaluation value, such as "like", indicating that the image reading is good and is highly valued. The advanced-level radiologist evaluates the presence/absence of "approval" and "like" by, for example, applying a check in a check box relating to an entry of the novice radiologist in charge.

In step S133, a display control function 117 displays transitions of the "implementation time" and the "like" evaluation by a graph with reference to an image reading implementation record at any period. Here, a modality, a site, and a disease, etc. can be used for grouping items relating to the preparation of the graph. An example of the transition of the image reading implementation time will be described later in FIG. 15 and FIG. 16, and an example of the transition of the like evaluation will be described later in FIG. 17.

In step S134, a management function 111 refers to the above graph and changes the "weighting" and the "proficiency attainment time" in a preferred image reading type table 500. For example, in a case of receiving an instruction from a manager to increase the weighting of a novice radiologist who is to be prioritized in being assigned an image reading order, the management function 111 changes the weighting of the novice radiologist in accordance with the instruction. An example of the revised preferred image reading type table 500 will be described later in FIG. 18.

In step S135, the management function 111 refers to the above graph and changes a "predicted time" corresponding to the work cost in a radiologist assignment table 110. For example, in a case where it is determined that the implementation time of the novice radiologist is shortened, and the evaluation made by the advanced-level radiologist is rising, the predicted time of the novice radiologist is changed from a "novice" level to a "middle ranking" level in a time for preparing image reading report table 400. An example of the revised radiologist assignment table 110 after the change will be described later in FIG. 19.

An example of a diagram relating to an operation of the task assignment supporting apparatus according to the second embodiment will be explained with reference to FIG. 14 to FIG. 19.

FIG. 14 shows an example of the record of image reading implementation table 140 recording the implementation time and the evaluation of the image reading. In the record of image reading implementation table 140, a "task ID" which is a management number for uniquely identifying a task, an "order number" which is a management number of an image reading order, a "modality" indicating the type of medical image diagnostic device acquiring original data of an image to be read, a "site" and a "disease" of a patient shown in an image to be read, a "doctor in charge" who is in charge of the image reading, a "preceding task" indicating whether or not the image reading is performed with respect to a same image, an "implementation time" indicating a time actually required for the image reading, an "approval" indicating that the report is approved as the image reading report, and a "like" indicating that the image reading is good and is highly valued, are stored in an associated manner. As for the "disease", a disease that is found as a result of the image reading may be input.

For example, in the first row of the entry of the record of image reading implementation table 140, task ID "3", order number "3", modality "MR", site "liver", disease "liver cirrhosis", doctor in charge "novice A", preceding task "Null", implementation time "35 min", approval "checked", and like "checked" are stored in an associated manner.

Figure 15:
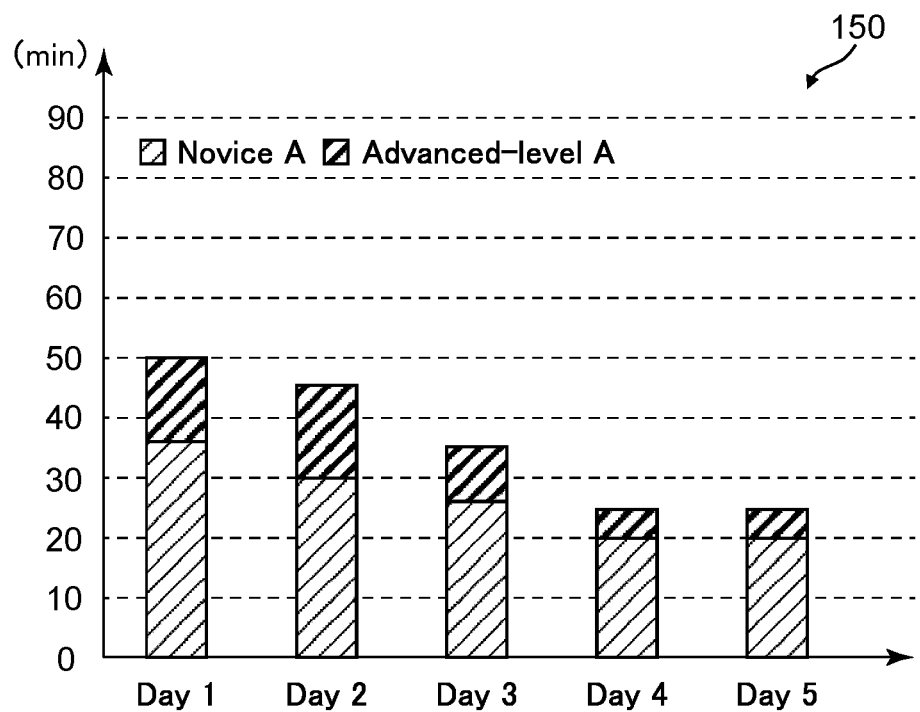
FIG. 15 shows an example of an image reading implementation temporal transition.

FIG. 15 shows an example of an image reading implementation temporal transition 150 indicating a transition of an image reading implementation time. In the image reading implementation temporal transition 150, a horizontal axis indicates the number of days or date, and the vertical axis indicates an implementation time. Here, the implementation time of a novice A and an advanced-level A is expressed by a stacked bar graph. It should be noted that any display method may be used as long as the corresponding relationship between the number of days or date and the implementation time is explicitly described.

Figure 16:
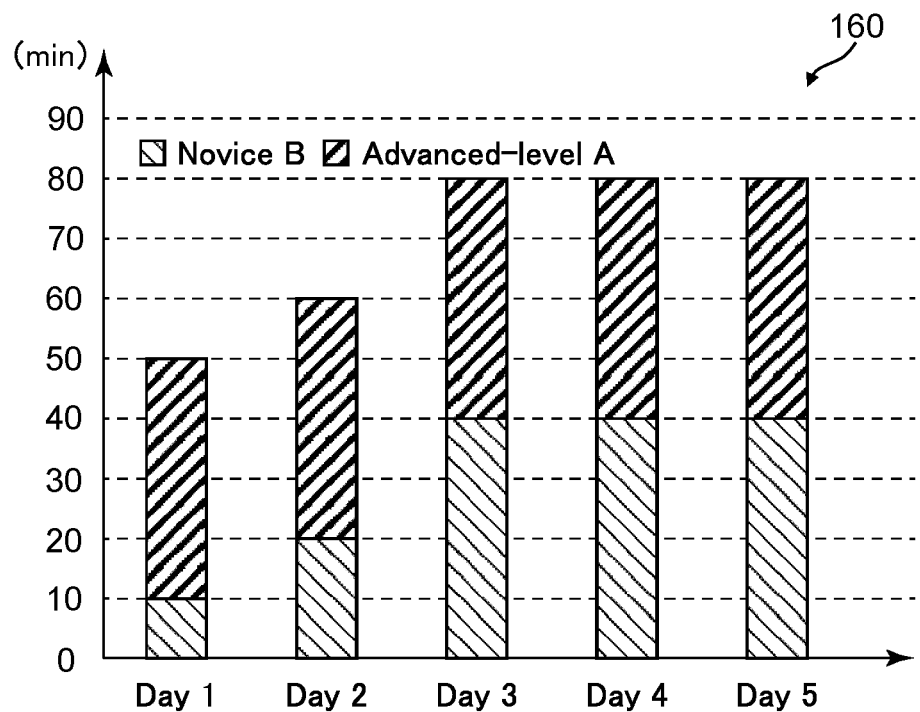
FIG. 16 shows an example of an image reading implementation temporal transition.

FIG. 16 shows an example of an image reading implementation temporal transition 160 indicating a transition of an image reading implementation time. Here, the implementation times of a novice B and an advanced-level A are expressed by a stacked bar graph.

For example, according to the image reading implementation temporal transition 150, an image reading time of "Day 1" consists of novice A "35 min" and advanced-level A "15 min", and an image reading time of "Day 5", after several days, consists of novice A "20 min" and advanced-level A "5 min". On the other hand, according to the image reading implementation temporal transition 160, an image reading time of "Day 1" consists of novice B "10 min" and advanced-level A "40 min", and an image reading time of "Day 5", after several days, consists of novice B "40 min" and advanced-level A "40 min".

According to FIG. 15 and FIG. 16, after several days from the first day, the image reading time of novice A has decreased, and the checking time of advanced-level A has also decreased. Therefore, it may be considered that the proficiency level of novice A relating to the image reading has increased, and that the skill has improved. On the other hand, after several days from the first day, the image reading time of novice B has increased, and the checking time of advanced-level A has not decreased. Therefore, it may be considered that the proficiency level of novice B relating to the image reading has not increased, and that the skill has not improved.

FIG. 17 shows an example of a like evaluation transition 170 indicating the transition of a like evaluation. In the like evaluation transition 170, a horizontal axis indicates the number of days or date, and the vertical axis indicates the number of likes evaluation. Here, the number of likes evaluation for each of novice A and novice B is expressed by a line graph. Specifically, novice A is expressed by a solid line, and novice B is expressed by a broken line. It should be noted that any display method may be used as long as the corresponding relationship between the number of days or date and the like evaluation is explicitly described.

For example, according to the like evaluation transition 170, the like evaluations of "Day 1" are novice A "1" and novice B "1", and the like evaluations of "Day 5", after a several days, are novice A "5" and novice B "2".

FIG. 18 shows an example of a revised preferred image reading type table 180 showing the preferred image reading type table 500 after revision based on statistical results of FIG. 15 to FIG. 17. In the revised preferred image reading type table 180, for the sake of convenience of explanation, cells of which the input values are revised are shaded to emphasize the revised portions.

In a case where it is determined that there is more prospect in the growth of novice A than in the growth of novice B, for example, according to the revised preferred image reading type table 180, the weighting will be changed from novice A and novice B "1" to novice A "10" and novice B "0.5", respectively. Furthermore, as for novice B, since the implementation time of image reading and the checking time of the advanced-level radiologist have not decreased, it is determined that the growth of novice B may take more time than was originally expected. Therefore, the proficiency attainment time of novice B may be changed to "middle ranking" "2100/3/25" and "expert" "2100/3/25".

FIG. 19 shows an example of a revised radiologist assignment table 190 showing the radiologist assignment table 110 after revision based on statistical results of FIG. 15 to FIG. 17. In the revised radiologist assignment table 190, for the sake of convenience of explanation, cells of which the input values are revised are shaded to emphasize the changed portions.

As for novice A, since the implementation time of image reading has decreased, for example, according to the revised radiologist assignment table 190, the predicted times "40 min" and "20 min" of novice A and advanced-level A, respectively, are revised to novice A "30 min" and advanced-level A "15 min".

It should be noted that although a like evaluation is listed as an example of an evaluation item in the record of image reading implementation table 140, it is not limited thereto. For example, a negative evaluation item such as "bad" may be added to a positive evaluation item such as the like evaluation, or only a negative evaluation item may be set. Furthermore, an item may also be set to comment on which content of the image reading report is good or bad in detail.

Furthermore, in the record of image reading implementation table 140, the image reading report which has received "approval" may be counted as having been prepared, and the image reading report which has not received "approval" may not be counted as having been prepared. The total cumulative number of approvals may also be managed in association with the radiologist in the radiologist request classification table 500. In such a case, when the number of approvals reaches the reference number of cases of middle ranking or expert in the number of prepared image reading reports table 300, the novice radiologist may be promoted to middle ranking or expert. Here, the promoted date may also be associated and managed in the preferred image reading type table 500.

Furthermore, the changes to the nurturing policy of the novice radiologist caused by the changes in the weighting and the proficiency attainment time may be made manually by the manager or automatically by an artificial intelligence (AI). Specifically, a trained model that has been trained by having the "implementation time" and the "like evaluation" in the record of image reading implementation table 140 as an input and at least one of the "proficiency attainment time" and the "weighting" in the preferred image reading type table 500 or the "predicted time" in the radiologist assignment table 110 as an output may be used. By using the trained model, at least one of the proficiency attainment time, the weighting, or the predicted time, which have been changed based on the implementation time and the like evaluation, can be obtained.

Furthermore, by establishing a corresponding relationship between the proficiency attainment time and the weighting, a change made to one of the proficiency attainment time or the weighting may influence the other to be changed dependently. Here, the change may be made by a GUI such as a slider.

An example of a manager changing the nurturing policy of a novice radiologist based on the implementation time of the novice radiologist and the evaluation from an advanced-level radiologist without disclosing it to the novice radiologist has been explained. However, it is not limited thereto. For example, by disclosing the evaluation to the novice radiologist, the growth of the novice radiologist may be motivated.

According to the second embodiment described above, by visualizing the transitions of the implementation time relating to a novice doctor to perform a medical care task and the checking time of an advanced-level doctor, the task load on each doctor can be confirmed. Additionally, by visualizing the transition of the evaluation made by an advanced-level doctor to a novice doctor, the characteristics and nurturing state of the novice doctor can be confirmed. Furthermore, by feeding back accomplishments of the novice doctor and the advanced-level doctor successively, in addition to being able to change the nurturing policy of the novice doctor based on the hospital policy in consideration of the current status, the task load on each doctor can be optimized.

It should be noted that the form of implementation may be a program that realizes the operation of the above embodiment. That is, after the program is stored in a storage region of other systems or devices, the program may be read out and executed by processing circuitry.

According to at least one of the embodiments explained above, the skill of a novice doctor may be encouraged to improve in accordance with a career desired by the novice doctor and the hospital policy, and the task load of doctors in general can be optimized.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A task assignment supporting apparatus, comprising:
processing circuitry configured to
store, in a memory, information of types of image reading preferences indicating types of image reading tasks preferred by each radiologist, of a plurality of radiologists, and a proficiency attainment time relating to each radiologist, the proficiency attainment time being set for each radiologist;
acquire an image reading order and a type of image reading order indicating a type of image reading task required for the image reading order;
assign to the image reading order, by accessing the stored information in the memory, a radiologist with a type of image reading preference corresponding to the type of image reading order;
change an assignment ratio of a number of image reading orders among the plurality of radiologists when assigning the plurality of radiologists to a plurality of image reading orders, in accordance with a remaining period left until the proficiency attainment time for each of the plurality of radiologists; and
update the proficiency attainment time for at least one of the plurality of radiologists based on an output of a trained artificial intelligence model.

2. The task assignment supporting apparatus according to claim 1, wherein the processing circuitry is further configured to
store, in the memory, a reference value of an image reading time relating to the acquired image reading order, and
assign the radiologist in a manner such that a work cost of the radiologist does not exceed a threshold value, the work cost being calculated based on the stored reference value of the image reading time.

3. The task assignment supporting apparatus according to claim 1, wherein the processing circuitry is further configured to
store, in the memory, a reference value of a number of image readings relating to the image reading order, and
change the assignment ratio of the number of image reading orders when assigning the plurality of radiologists to the plurality of image reading orders, further in accordance with a remaining number of cases left until the reference value of the number of image readings.

4. The task assignment supporting apparatus according to claim 1, wherein the processing circuitry is further configured to
store, in the memory, weighting relating to the radiologist, and
change the assignment ratio of the number of image reading orders when assigning the plurality of radiologists to the plurality of image reading orders, further in accordance with the weighting.

5. The task assignment supporting apparatus according to claim 1, wherein the processing circuitry is further configured to calculate the proficiency attainment time based on at least one of a number of image readings per unit period, a reference value of a number of image readings, or a weighting.

6. The task assignment supporting apparatus according to claim 1, wherein the processing circuitry is further configured to assign, after assigning a first radiologist with a type of image reading preference corresponding to the type of image reading order, a second radiologist with a higher proficiency than the first radiologist to the image reading order.

7. The task assignment supporting apparatus according to claim 6, wherein the processing circuitry is further configured to assign the second radiologist to an urgent image reading order, without assigning the first radiologist.

8. The task assignment supporting apparatus according to claim 1, wherein the processing circuitry is further configured to
store, in the memory, a first type of image reading preference indicating a type of an image reading task preferred by a first radiologist for each of the first radiologists, and store, in the memory, a second type of image reading preference indicating a type of an image reading task preferred by a second radiologist for each of the second radiologists with a higher proficiency than the first radiologists, and
assign, to the image reading order, the second radiologist with the second type of image reading preference corresponding to the type of image reading order.

9. The task assignment supporting apparatus according to claim 1, wherein the processing circuitry is further configured to
record an implementation time required for the image reading task and an evaluation with respect to a processing result of the acquired image reading order, and
display a transition of at least one of the implementation time or the evaluation.

10. The task assignment supporting apparatus according to claim 9, wherein the evaluation recorded by the processing circuitry includes a good/bad evaluation with respect to the processing result of the image reading order.

11. The task assignment supporting apparatus according to claim 9, wherein based on at least one of the implementation time or the evaluation, the processing circuitry is further configured to change at least one of a predicted time required for reading an image of the image reading order, the proficiency attainment time relating to the radiologist, or a weighting relating to the radiologist.

12. The task assignment supporting apparatus according to claim 9, wherein the processing circuitry is further configured to use a trained model, which has at least one of the implementation time or the evaluation as an input, and has at least one of a predicted time required for reading an image of the image reading order, the proficiency attainment time relating to the radiologist, or a weighting relating to the radiologist as an output.

13. A task assignment supporting system including an ordering system and a task assignment supporting apparatus, wherein
the ordering system manages an image reading order and a type of image reading order indicating a type of image reading task required for the image reading order, and
the task assignment supporting apparatus comprises processing circuitry configured to:
store, in a memory, information of types of image reading preferences indicating types of image reading tasks preferred by each radiologist, of a plurality of radiologists, and a proficiency attainment time relating to each radiologist, the proficiency attainment time being set for each radiologist;
acquire the image reading order and the type of image reading order;
assign to the image reading order, by accessing the stored information in the memory, a radiologist with a type of image reading preference corresponding to the type of image reading order;
change an assignment ratio of a number of image reading orders among the plurality of radiologists when assigning the plurality of radiologists to a plurality of image reading orders, in accordance with a remaining period left until the proficiency attainment time for each of the plurality of radiologists; and
update the proficiency attainment time for at least one of the plurality of radiologists based on an output of a trained artificial intelligence model.

14. A task assignment supporting method, comprising:
storing in a memory, information of types of image reading preferences indicating types of image reading tasks preferred by each radiologist, of a plurality of radiologists, and a proficiency attainment time relating to each radiologist, the proficiency attainment time being set for each radiologist;
acquiring an image reading order and a type of image reading order indicating a type of image reading task required for the image reading order;
assigning to the image reading order, by accessing the stored information in the memory, a radiologist with a type of image reading preference corresponding to the type of image reading order;
changing an assignment ratio of a number of image reading orders among the plurality of radiologists when assigning the plurality of radiologists to a plurality of image reading orders, in accordance with a remaining period left until the proficiency attainment time for each of the plurality of radiologists; and
update the proficiency attainment time for at least one of the plurality of radiologists based on an output of a trained artificial intelligence model.

* * * * *